(12) United States Patent
Spartz et al.

(10) Patent No.: US 10,401,336 B2
(45) Date of Patent: Sep. 3, 2019

(54) METHOD AND SYSTEM FOR LOW TEMPERATURE DETECTION OF SEMI VOLATILE ORGANIC COMPOUNDS

(71) Applicant: MLS ACQ, Inc., East Windsor, CT (US)

(72) Inventors: Martin L. Spartz, Ellington, CT (US); Alice Elizabeth Delia, Mt. Pleasant, MI (US); Peter Paul Behnke, Vernon, CT (US); Charles Mark Phillips, Sicklerville, NJ (US)

(73) Assignee: MLS ACQ, INC., East Windsor, CT (US)

( * ) Notice: Subject to any disclaimer, the term of this patent is extended or adjusted under 35 U.S.C. 154(b) by 62 days.

(21) Appl. No.: 15/852,655

(22) Filed: Dec. 22, 2017

(65) Prior Publication Data

US 2018/0180579 A1    Jun. 28, 2018

Related U.S. Application Data

(60) Provisional application No. 62/438,304, filed on Dec. 22, 2016.

(51) Int. Cl.
*G01N 30/02* (2006.01)
*G01N 30/74* (2006.01)
(Continued)

(52) U.S. Cl.
CPC .............. *G01N 30/74* (2013.01); *G01N 1/22* (2013.01); *G01N 21/05* (2013.01); *G01N 30/14* (2013.01);
(Continued)

(58) Field of Classification Search
CPC ................ G01N 30/74; G01N 30/743; G01N 3030/746; G01N 30/02; G01N 2030/027; G01N 2030/121; G01N 2030/123; G01N 30/32; G01N 2030/326; G01N 2030/621; G01N 2030/623; G01N 2030/626;
(Continued)

(56) References Cited

U.S. PATENT DOCUMENTS 4,007,626 A * 2/1977 Roof ....................... G01N 30/12
                                                                         73/19.02
5,997,615 A * 12/1999 Luong .................... G01N 30/12
                                                                         96/105
(Continued)

OTHER PUBLICATIONS

De Kruif, C.G., "Enthalpies of sublimation and vapour pressures of 11 polycyclic hydrocarbons," J. Chem. Thermodynamics, 12(3): 243-248 (1980).

*Primary Examiner* — Robert R Raevis
(74) *Attorney, Agent, or Firm* — HoustonHogle LLP

(57) ABSTRACT

A sample analysis method includes directing a sample that contains one or more SVOC components to a GC column to temporally separate components present in the sample. Output gas from the GC column is expanded into a sample cell. The sample cell is held at a temperature and pressure that are lower than the temperature and pressure at an outlet of the GC column. The volume of the sample cell is sufficiently large for maintaining the one or more SVOC components in a gaseous phase. Infrared spectra of the components in the sample cell are obtained using a Fourier transform infrared spectrometry system.

17 Claims, 1 Drawing Sheet

(51) Int. Cl.
  *G01N 30/14* (2006.01)
  *G01N 1/22* (2006.01)
  *G01N 21/05* (2006.01)
  *G01N 30/12* (2006.01)
  *G01N 30/30* (2006.01)
  *G01N 1/42* (2006.01)
  *G01N 21/35* (2014.01)

(52) U.S. Cl.
  CPC ....... *G01N 1/42* (2013.01); *G01N 2021/3595* (2013.01); *G01N 2030/025* (2013.01); *G01N 2030/128* (2013.01); *G01N 2030/143* (2013.01); *G01N 2030/3038* (2013.01); *G01N 2030/743* (2013.01)

(58) Field of Classification Search
  CPC ............. G01N 30/14; G01N 2030/884; G01N 2030/8845; G01N 2030/885; G01N 2030/8854; G01N 1/22; G01N 2030/743; G01N 2030/128; G01N 2030/143; G01N 2030/3038; G01N 2030/025; G01N 1/42; G01N 2021/3595
  USPC ...................... 73/23.37, 1.06, 23.22; 422/89; 96/82–89; 436/161
  See application file for complete search history.

(56) References Cited

U.S. PATENT DOCUMENTS

| 9,606,088 B2 | 3/2017 | Spartz et al. |
| 2017/0122920 A1 | 5/2017 | Spartz et al. |

\* cited by examiner

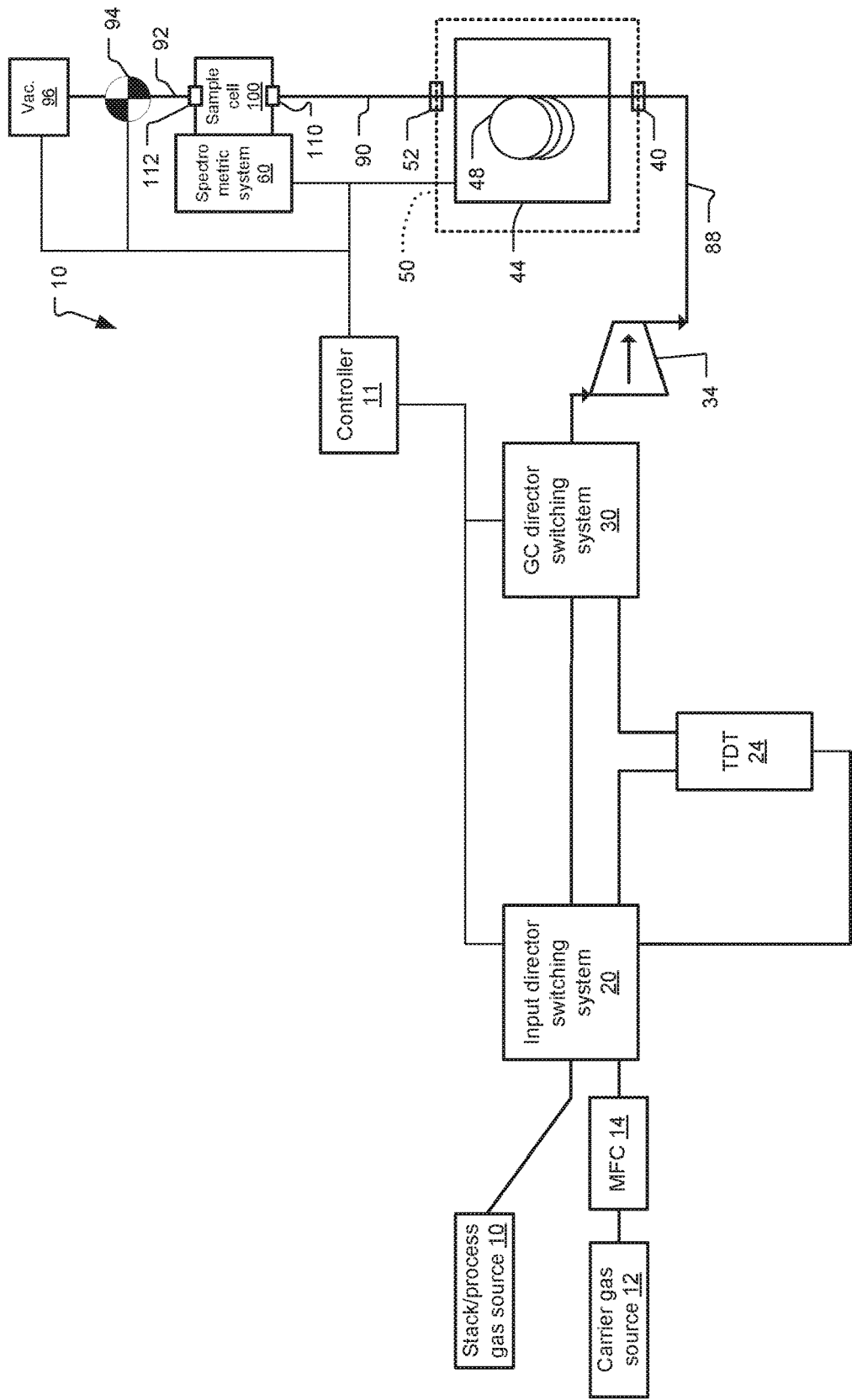

METHOD AND SYSTEM FOR LOW TEMPERATURE DETECTION OF SEMI VOLATILE ORGANIC COMPOUNDS

RELATED APPLICATIONS

This application claims the benefit under 35 USC 119(e) of U.S. Provisional Application No. 62/438,304, filed on Dec. 22, 2016, which is incorporated herein by reference in its entirety.

BACKGROUND OF THE INVENTION

Gas chromatography (GC) is an analytical method that measures the content of various components in a sample. The method for separating chemical substances relies on differences in partitioning behavior between a flowing mobile phase (gas phase) and a stationary phase supported in a column to separate the components in a mixture. As the gas flow passes through the column, the sample components move at velocities that are influenced by the degree of interaction of each component with the stationary phase in the column. Consequently, the different components separate in time as the components elute from the column.

While GC is widely used to resolve a mixture into its various components according to retention profiles of the different molecules passing through the GC column, and can potentially handle mixtures containing large numbers (hundreds, for instance) of substances, identifying the molecules that elute from the column is more problematic. For example, full peak separation is often needed to qualify and quantify the compounds present. Small sample sizes and dynamic ranges, and the need for continuing calibration are additional drawbacks.

To address the need for rapid and sensitive identification of the molecular species present, GC has been integrated with techniques such as mass spectrometry (MS) or Fourier transform infrared (FTIR) spectrometry.

Gas chromatography-mass spectrometry (GC-MS) is probably the most widespread tandem technique in the analytical instrumentation industry today. GC-MS systems are versatile and are employed across many different industries, particularly for environmental, chemical, petroleum, pharmaceutical, and toxicological applications. While GC-MS is a fast, sensitive technique suitable for multiple component detection and spectral identification, capable of measuring atomic species and supported by large available spectral libraries, it suffers from some disadvantages. These include compound separation to prevent MS interferences, non-linear calibrations, poor precision and accuracy (requiring constant calibration) and limited dynamic range. Problems also are encountered when high concentrations are present that can allow for chemical ionization to occur, generating questionable data.

While GC-MS is the more commonly deployed solution, Gas Chromatography-Fourier Transform Infrared Spectrometry (GC-FTIR) provides a powerful analytical tool that is particularly useful to distinguish among structural isomers that have identical electron impact and chemical ionization mass spectra.

Nevertheless, historically the designs of GC-FTIR systems have been plagued with their own limitations. For example, many GC-FTIR sample cells utilize a "light pipe" (typically a cell or cuvette used for passing both gas eluted from the GC column, and light from the FTIR interferometer). The light pipe is made relatively short to prevent peak dilution through the IR cell and its eventual IR detection or secondary detection. Since IR absorption is proportional to cell path length, this short path length limits the sensitivity (minimum detection limit (MDL)) of the technique. Problems also arise in cases in which GC peaks come off very quickly. Since the light pipe has a relatively large volume when compared to the flow rates of the GC, the gas can become diluted, making measurements more difficult.

More recently, Spartz, et al., in U.S. Pat. Appl. Pub. No. US 2015/0260695 A1, now U.S. Pat. No. 9,606,088, issued Mar. 28, 2017, both of which are incorporated herein by this reference in their entirety, disclose GC-FTIR techniques and systems with the objective of coupling existing or newly developed approaches, such as GCs, and/or optical spectroscopy systems (e.g., FTIRs) in ways that reduce or minimize the deficiencies encountered with conventional arrangements. According to U.S. Pat. No. 9,606,088, FTIR techniques, typically implemented by software executed by a computer are employed to identify unknown compounds present in a sample. The techniques can be applied or adapted to any analysis process or instrumentation that uses a FTIR spectrometry system or another suitable spectrometry system. In many cases, the spectroscopic analysis is further enhanced or facilitated by a temporal separation of unknown compounds present in the sample being analyzed. In specific implementations, the separator is a GC.

U.S. patent application Ser. No. 15/335,618, filed on Oct. 27, 2016, published on May 4, 2017 as U.S. Patent Application Publication No. 2017/0122920 A1, and incorporated herein by this reference in its entirety, outlines, in more detail, a switching systems upstream and downstream of thermal desorption tubes, the GC, and the spectrometry (e.g., FTIR) system sample cell. Arrangements and techniques disclosed in this document include, for example, a spectrometry system for detecting components of a sample; a gas chromatography column for separating the components of a sample; a first sample unit for receiving a first sample from a sample source; and a second sample unit for receiving a second sample from a sample source. Each sample loop unit allows independent processing of samples in preparation for analysis.

SUMMARY OF THE INVENTION

Traditionally, during GC analyses, it has been necessary to maintain the GC detector at a sufficiently high temperature to prevent condensation as the gas emerging from the GC column. Additional challenges can be encountered when this gas contains semi volatile organic compounds, also known as SVOCs, since this subgroup of volatile organic compounds (VOCs) is typically characterized by higher molecular weights and higher boiling point temperatures.

Having to heat the FTIR sample cell to temperatures sufficient to maintain SVOCs above their normal boiling point may complicate the sample analysis process. For example, since compounds often have IR absorption spectra that depend on temperature, raising the temperature of the sample cell would require generating additional calibrations at one or more new (typically higher) temperatures.

Problems also can be encountered with sample cells configured for multiple path absorption and employing gold-based optics. Since it is known that the reflectivity of gold decreases with increased temperatures, light losses associated with the higher temperatures needed when handling SVOCs can have a negative impact on detection limits.

Thus, a need continues to exist for approaches that can circumvent or supplement the high GC detector temperature requirements encountered when handling SVOCs.

In the analysis system and method described herein, condensation in the sample cell is prevented or minimized by expanding the gas from the small volume it occupies before emerging from a GC column to a larger volume presented by an appropriately configured sample cell. The expansion effects a drop in the vapor pressure of the analyte. As a consequence, SVOC analytes can remain in their vapor phase even when the gas cell is held at a temperature below their normal boiling point (defined as the temperature at which a liquid boils at 1 atmosphere of pressure).

In one aspect, the invention features a sample analysis method that includes directing a sample that contains one or more SVOC components to a GC column to temporally resolve or separate components present in the sample; and expanding output gas from the GC column into a sample cell. The sample cell is held at a temperature and pressure that are lower than the temperature and pressure at an outlet of the GC column. The volume of the sample cell is sufficiently large for maintaining the one or more SVOC components in a gaseous phase. The method also includes obtaining IR spectra of the components in the sample cell with a Fourier transform infrared spectrometry system. In many cases, the volume of the sample cell is at least 200 times larger than an initial volume available to the output gas before exiting the outlet of the GC column.

By practicing approaches described herein, the sample cell can be operated at lower temperatures than otherwise needed to maintain SVOCs in the vapor (gas) phase. This is particularly advantageous in cells that utilize gold-coated optics, since it is known that as the temperature rises, the reflectivity of gold decreases. With a multiple path cell design, a modified White cell, for example, that includes gold reflecting optics, a lower cell temperature can result in more light passing through the cell and, potentially, to lower detection limits.

Also, since IR gases have absorption spectra that depend on temperature, it is advantageous to choose a single temperature at which to operate the detector (sample cell) so that the collected sample spectra are only measured at one temperature and will match the quantified spectral library without having to vary the gas cell temperature with time or for a specific list of compounds.

Techniques described herein provide flexibility in how the sample cell is operated. While in many cases a preferred temperature for the gas cell may be 191° C., the cell can be heated as needed, to a temperature of about 200 or 250° C., for example. Spectral calibrations could be collected at the higher temperature, as needed.

Some of the approaches described herein are associated with lower costs and/or simplified procedures. In cases in which thermal desorption tubes (TDTs) are employed, these devices can be packed with inexpensive materials. In addition to realizing costs benefits, a packing that is nothing more than glass wool, for example, will not trap VOCs or water. In the absence of VOCs and/or water, much larger samples containing SVOCs can be collected on the TDT.

It is also possible to bypass solvent extraction steps traditionally used to prepare samples containing SVOCs, thus simplifying the process, reducing the cost of materials as well as waste disposal requirements.

For configurations described in U.S. Pat. No. 9,606,088 and/or U.S. Patent Application Publication No. 2017/0122920 A1, if a compound were to enter the gas cell and condense, it would be observed in the spectra due to a loss of the compound with time, resulting in a negative peak.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

The FIGURE is a schematic diagram of a GC-FTIR sample analysis system for detecting and measuring contaminants such as VOCs or SVOCs.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

In many of its aspects, the invention relates to approaches for analyzing a sample. In typical applications, the sample is a mixture containing more than one distinct chemical species. Techniques described herein are particularly well suited for the analysis of samples that contain one or more compounds having a relatively high normal boiling point, i.e., the boiling point at a pressure of 1 atmosphere (also known as atmospheric pressure), such as, for example, semi volatile or nearly non-volatile organic compounds, as well as other compounds that are weakly volatile. Such compounds are collectively referred to herein as "SVOCs". Examples include pesticides, herbicides, insecticides, plasticizers, flame retardants, phthalates, mycotoxins, PCBs, illicit drugs, explosives or accelerants. Specific compounds classified as SVOC can be found in lists provided by regulatory agencies such as, for example, the Environmental Protection Agency (EPA). See, e.g., EPA Method 8270D (SW-846), used to determine the concentration of semi volatile organic compounds in extracts prepared from many types of solid waste matrices, soils, air sampling media and water samples by GC-MS.

As described in U.S. Pat. No. 9,606,088, components in the sample can be separated through various suitable techniques. In a GC column, for example, compounds in a mixture become separated based on their flow rates. Typically, lighter gases will elute through a column quicker than heavier ones. Thus, the GC column allows the FTIR system to differentiate substances with similar looking spectra using time. The electromagnetic-based radiation spectroscopic device (an FTIR spectrometry system, for example) can be used to identify and, in many cases, quantify the species present, resolved temporally by the separator.

The GC and/or FTIR spectrometer can be commercially available instruments, with exhaust from the GC being often directly coupled to the FTIR sample cell.

An example of a system that includes a separator for temporally resolving components in a sample, e.g., a gas chromatograph, a sample cell and a spectrometer, e.g., FTIR or dispersive or tunable source spectrometer, which includes a light, and more generally, an electromagnetic (EM) radiation source is shown in FIG. 1 of U.S. Pat. No. 9,606,088. Controls, automation instrumentation, computer interfaces, algorithms and/or software-related features also are described, as are various techniques for carrying out sample analyses.

In general, the GC uses a stationary phase, which is typically a microscopic layer of liquid or polymer on an inert solid glass or metal tube, i.e., a column. The mobile phase is a carrier gas, usually an inert gas such as helium or a non-reactive gas such as nitrogen, for instance ultra high purity (UHP) $N_2$. Other carrier gases or gas mixtures can be utilized, as known in the art.

The carrier gas flow is controlled by flow controllers and/or a series of valves to maintain or vary the flow rate during the separation. The flow controllers and valves can also be used to allow the entire sample or a fraction of the sample to enter the column. Typically, the column is located in an oven where the temperature of the gas passing through the column can be controlled. The gaseous compounds interact with the walls of the column or stationary phase, causing each compound to elute at a different time, known as the retention time of the compound.

If analytes are present in the sample at very low levels they can be concentrated prior to being separated using, for instance, one or more thermal desorption tubes (TDT), cold or cryo traps, etc. Use of such devices is described, for example, in U.S. Patent Application Publication No. 2017/0122920A1. See, e.g., TDT 72 and 78 in FIG. 1 of this document.

Output from the separator (e.g., GC), typically in a gaseous state that contains one or more gases and/or vapors, is directed to a sample cell.

The sample cell also receives electromagnetic radiation, for instance from light generated in the FTIR arrangement and can be designed to fit in the sample compartment of a commercial FTIR or other type of spectrometer. Output radiation exits the sample cell and can be directed by a reflector to a suitable detector, for instance a MCT (mercury cadmium telleride) device designed for measuring the light in an FTIR. Specific examples employ liquid nitrogen cooled MCTs. A suitable detector for a broad spectral analysis capability can be a 1 mm mid-band MCT with a cutoff of 16 µm.

To allow transmission of an electromagnetic radiation beam within a desired wavelength (or frequency) range into and out of the sample cell, the optical components used, e.g., windows, are selected according to their performance at that specific range. For instance, suitable materials that can transmit IR radiation include potassium bromide (KBr), potassium chloride (KCl), cesium iodide (CsI), barium fluoride ($BaF_2$), sodium chloride (NaCl), calcium fluoride ($CaF_2$), magnesium fluoride ($MgF_2$), zinc selenide (ZnSe), zinc sulfide (ZnS), thallium bromoiodide (KRS-5), silver chloride (AgCl), silver bromide (AgBr), lithium fluoride (LiF), sapphire, diamond, silicon, germanium, fused silica, AMTIR-1 ($Ge_{33}AS_{12}Se_{55}$) and various silicon, cadmium, selenium and germanium based glasses and many others, as known in the art.

The sample cell can be configured for multiple-path (also known as multiple-pass or long path) absorption. By increasing the path length traveled, multiple-pass arrangements can be used to measure low concentration components or to observe weak absorption spectral features without increasing the physical length or volume of the cell itself. Since the detection limit of the system is directly related to the volume/path length ratio, decreasing the volume or increasing the path length lowers the concentrations that can be detected. Assuming no signal losses, doubling the path length or reducing the volume in half will lower the MDL by a factor of 2.

Many applications employ gold coatings. In other embodiments, longer path lengths are used in combination with higher reflective coatings like enhanced silver, yielding a reflectivity in the 0.992 to 0.995 range or greater. Coating optimizations, in the IR region, for example, could further improve reflectivity, e.g., by a factor or 4 to 8 or even more.

In specific implementations, the sample cell is configured as a "White cell" type. In a traditional White cell arrangement, three spherical concave mirrors are employed having the same radius of curvature. Second generation multiple-path gas cells can use non-spherical concave mirrors to improve image quality and optical throughput. In one example, the White cell type employed uses non-spherical concave mirrors cut onto a single metal or a glass blank, providing a fixed path length; the mirrors can be the solid end caps of the sample cell, allowing for smaller sample cells that are easier to align.

Furthermore, the modified White cell can be a fixed path cell, with no adjustment for path length. Such a design reduces the number of variables to be monitored and/or controlled. In one instance, the White type cell has a volume of ~200 mL. Using gold mirrors can produce a path length of about 5.11 meters (m); enhanced silver mirrors can result in path lengths of 10 m or much longer. This increase in path length and change from gold to silver improves the throughput of the gas cell and provides an approximate doubling or more of the absorption signal which further reduces the analyte MDLs.

Other multiple pass cell designs can be utilized. Examples include but are not limited to Herriott cells, Pfund cells, cavity-ring down cells, and integrating spheres. A lightpipe flow sample cell can be utilized in some situations.

The sample cell can be heated using any suitable device, such as, for example, heating tape, heating jackets, ovens, Peltier heaters, cartridge heaters, immersion heaters, and so forth. In many embodiments described herein, the gas cell is operated at a temperature of about 191° C.

In some arrangements, the sample cell is designed to maintain a gas pressure lower than the surrounding (atmospheric or ambient) pressure to integrate the sample over time. In specific implementations, the pressure in the sample cell is within the range of about 0.001 to about 1.0 atm. For instance, a flow rate of 1 mL/minute, a sample cell volume of 200 mL and a starting gas cell pressure of ½ atmosphere can provide a 100-minute time period for data acquisition. This is considered a sufficient time window for most GC sample analyses. The pressure in the sample cell can be reduced with a vacuum pump, or alternative apparatus capable of drawing a vacuum.

In some cases, no vacuum is required and the system can be operated at a suitable pressure. For instance, a compressor or column head pressure could be used to compress or flow the output from the GC into and possibly through the sample cell. Preferably, over pressurizing is avoided.

The pressure in the sample cell can be monitored with a sensor, such as an absolute pressure sensor.

The system includes electronics and computer systems and video displays for the computer systems. It can further include additional computer systems, devices, units, interfaces, data co-processors, and/or other components for data processing, analysis (including multivariate qualitative and quantitative), recording, reporting, equipment controls, automation, flow control and controllers, pressure sensors and controllers, heaters and temperature controllers, valves and vacuum generation technology, spectral libraries, and so forth. One or more processors, memory devices, and so on, are provided in the computer systems for executing processes of the present invention.

The computer systems and/or any associated components are configured for executing software for implementing embodiments of the present invention, allowing automated data handling and analysis based on processes described below.

In many embodiments the system maintains background infrared spectra that include infrared spectra from previously eluted components and analyzes currently eluting components with reference to the background infrared spectra. In specific examples, spectral responses of the components are acquired over time and current spectral responses are compared to a background that changes with time and comprises previously acquired spectral responses to identify and/or quantify newly generated components.

The FIGURE is a schematic diagram of an exemplary system that can be used or adapted to conduct embodiments described herein.

The analysis system 10 includes a separator 50 for separating a sample, such as a gas sample, into its components (e.g., separate compounds), a spectrometric system 60 for detecting the spectral response of those compounds in a sample cell 100, and a controller 11 that controls the system and uses the spectral information to identify the compounds of the sample and their concentrations.

The spectrometric system 60 can determine the spectral response of the compounds in sample cell 100 in one or more spectral regions: near-, mid- and/or far-infrared, visible, and/or ultraviolet (UV) (including vacuum ultraviolet (VUV)). Further, the spectrometric system can measure different characteristics, such as absorption spectra, emission (including blackbody or fluorescence) spectra, elastic scattering and reflection spectra, and/or inelastic scattering (e.g., Raman and Compton scattering) spectra of the compounds in the sample cell.

In the case of optical spectrometric systems, for example, different technologies can be employed. In Fourier transform infrared spectrometry (FTIR) systems, single beam spectra are generated by taking the raw interferograms from the FTIR spectrometer and then converting those interferograms to intensity versus wavenumber spectra. In other situations, spectra might be directly read-out as in the case where the spectrometric system 60 is a post dispersive system, which includes a broadband source and a spectrally resolving detector system. In other examples, spectrometric system 60 includes a tunable optical source (e.g., tunable laser) and a detector. Here, the spectral information is a function of the time response of the detector, in such a pre-dispersive system.

In general, spectrometric system 60 is preferably sufficiently sensitive so that by analysis of the spectral information, controller 11 can detect at least some of the sample compounds with low concentration, such as in a few percent to low parts per million (ppm) concentrations, or lower, to parts per billion (ppb).

In a specific embodiment, spectrometric system 60 is a FTIR system. Its sample cell 100, also referred to as "gas cell" 100 is provided with an inlet port 110 for receiving a separator line 90. The sample cell 100 of the spectrometric system 60 has an outlet port 112 for venting the sample cell contents through exit line 92. An exit valve 94 seals and/or controls the flow from the sample cell 100. A vacuum pump 96 can be provided after the exit valve 94 so that a vacuum or partial vacuum can be drawn on the sample cell 100.

The sample components are separated in time by separation system 50, which is preferably a gas chromatography system. The GC system has a gas chromatographic column 48. Often the column 48 is coiled in order to minimize overall size while maintaining sufficient tube or column length. Column 48 has a proximate end or inlet 40 for receiving sample from sample inlet line 88 and distal end or outlet 52 for directing resulting product through line 90 to the sample cell 100 for analysis in spectrometry system 60.

The column 48 is typically held within a temperature controlled chamber 44 with a heat source (oven), such as a heating coil that is thermostatically controlled by controller 11, in order to maintain a selected constant temperature during a gas chromatography analysis run. Typically, the heat source also provides sufficient heat to the chamber interior so that the temperature is sufficiently high to ensure that the sample reaches a gaseous state. In one implementation, the column 48 is resistively heated. This avoids the need for the oven. Specifically, column 48 is heated directly by passing a current through the metal column and monitoring the resistance to determine the temperature.

In many implementations, the GC system is designed for SVOCs instead of volatile organic compounds (VOCs).

If the compounds of interest are not sufficiently concentrated to be adequately identified and measured in analysis system 10, a sample can be first concentrated prior to separation. In these circumstances, the sample is passed through a concentrator 24, then separated in separation system 50 and then analyzed by spectrometric system 60. Examples of concentrators suitable for such purpose are thermal desorption tubes (TDT) or cold (cryo) traps. Further, if the sample contains trace concentrations, for example in the ppb or parts per trillion (ppt) range, a series of concentrators can be used in analysis system 10. Such configurations allow the same system to be employed for a wide variety of samples and sampling conditions.

In some implementations, TDT 24 is utilized to collect a sample containing volatile organic compounds (VOCs), solvent, e.g., water and SVOCs. The desorption process is conducted by burning off the first two, then focusing the analysis on the heavier components (e.g., the SVOCs), using a programmed approach. In other implementations, further described below, the TDT is designed to capture SVOCs but not water and/or VOCs.

A control circuit managed by one or more computer systems can be used to dynamically control the sample cell pressure. For instance, automated valves can be set to pull a vacuum on the sample cell before starting a run or drawing the components through a flow cell. Pressure levels in the cell can also be controlled automatically. In many cases, isolating the sample cell from the pump, thus allowing gas to accumulate in the sample cell, is also performed automatically. Automation can be used to set a desired carrier gas flow from the separator, e.g., the GC, into the sample cell, to isolate the cell from the carrier gas, to divert the carrier gas to any secondary pumping station, to switch the flow to the FTIR gas cell for sample collection, and so forth.

In one mode of operation, the sample flows through the gas cell 100 and out through the exit valve 94 and multiple spectra are obtained over time by the spectrometric system 60 that integrates the GC effluent sample analyte into the gas cell for a brief period and allows for the possibility of averaging a set of spectra for detection limit reduction, i.e., enhancing detection sensitivity. This can be thought of as an analysis process with flow-through integrating cell.

In another mode of operation, the vacuum pump 96 draws a vacuum on the gas cell 100 and then the exit valve 94 is shut. In this mode, the cell 100 integrates and collects compounds of a sample for a certain time period. Here, the sample cell 100 has been partially or fully evacuated at the beginning of the run. Then, fluid compounds, e.g., components in gaseous phase, are allowed to accumulate in sample cell 100, integrating their spectral signatures. Multiple spectra obtained over a time interval can then be averaged to best measure the integrated concentration in the sample cell. The first spectra are then used as the initial background spectrum and new spectra are obtained as new compounds flow into the integrating sample cell 100. The spectra of the new compounds are obtained by comparing the current spectra to the background spectra. Then this process is repeated. This approach can be thought of as an analysis process with a static fully integrating cell. Further details, including a description of techniques related to data acquisition, data handling and data analysis, can be found in U.S. Pat. No. 9,606,088, incorporated herein by this reference in its entirety.

System 10 further includes an input director switching system 20 and a GC director switching system 30 for controlling the flow of gases into and out of the TDT 24 and GC 50.

The input director switching system 20 is connected for receiving sample gas from source 10, which can be a process fluid or gas from a stack. In cases in which a sample is collected on TDT 24 in a different manner (off-line, for example, as in the case of some soil, dust, waste, air or water testing), the connection to the stack process gas source 10 can be bypassed.

Input director switch 20 also connects to a carrier gas source 12, such as nitrogen, helium or other essentially inert gas that will not interfere with detecting pollutants and other impurities. A mass flow controller (MCF) 14 is preferably provided in-line between the carrier gas source 12 and the input director 20 to control the flow rate of the carrier gas. The input director switching system 20 then selectively connects either of these two sources directly to the GC director switching system 30 or to the TDT 24.

GC director switching system 30 is connected for receiving sample or carrier gas from the input director switching system 20 or gas desorbing from the TDT 24. Output from director switching system 30 then provides gas to GC 50. Possibly a compressor 34 is provided inline between GC director switching system 30 and GC 50.

By control of the input director switching system 20 and the GC director switching system 30, a gas sample can be concentrated in the TDT and then desorbed into GC 50; or, the TDT 24 can be bypassed and the gas sample provided directly to GC 50.

In practice, the functions of controller 11 are often distributed among multiple computer systems. For example, one computer system will often perform the functions of real-time control of the system 10 and collecting and logging the data from the system 10. This includes controlling the flow of gases and liquids throughout the system 10 by controlling one or more MFCs, e.g., MFC 14, input director 20, GC director 30, collection and desorption of TDT 24, valves, e.g., exit valve 94, compressor 34, vacuum pump 96, and separator 50 in addition to the other components of system 10. The real-time control functions further include collecting and recording the spectral information from spectrometric system 60. Then, a second computer system will often be utilized to analyze that data and identify the specific compounds of the sample. This includes analyzing the spectral information and how that information changes over time and recording and reporting the components/compounds present with their concentrations or mass to an operator via a user interface or to another computer. These data are compared with known preset amounts of concentrations (e.g., determined in a calibration procedure) that the spectrometric system 60 is capable of detecting.

With respect to flow pattern of the carrier gas (e.g., $N_2$), it is possible to direct the flow from the GC into the sample cell continuously. If desired, the sample cell can be closed to the $N_2$ flow from the GC, for a given time interval. In yet other arrangements, the carrier gas, or the sample from the GC can be diverted to a secondary pumping service to prevent spectral interference from large concentration compounds such as solvent species. The flow can then be switched for sample collection. If pumping continues, the compounds that come off during this time will be standard chromatographic components (peaks) and their concentrations can be calculated as such. The peak will go up and go down as it enters and exits the sample cell so no further averaging may be needed.

If the sample cell is initially evacuated, then sealed from the pump, the carrier gas and sample components from the GC can accumulate in or flow through the sample cell and spectra can be obtained during the entire data collection. Since the chemicals are captured in the sample cell, the entire amount of each gas (compound) can be measured once it has completely eluted from the separation device (GC). Since the gas cell is a multiple pass gas cell in a one embodiment, there can be an increased absorption for each gas when compared to "light pipe" system in an optimized design. By letting all the gas remain in the gas cell, this in effect integrates the sample peak from a traditional analyzer where the sample moves past or through the detection system. This integration provides a further enhancement in SNR, which can be a factor of 2 to 5 times since the entire amount of sample is measured once it has completely eluted. Typically, this improvement is dependent on the width of the eluted peak.

The arrangements and techniques described above highlight the wide range of choices in how the gas cell is operated. It is possible, for example, to capture gas in the sample cell for a specific time, based on the gas turnover rate in cell. Various flow conditions can be employed. In a transient mode, for instance, the entire experiment (run) is conducted under a set, i.e., unchanging pressure, e.g., under a set vacuum pressure. In a full integration mode, the sample cell is evacuated and the sample is allowed to accumulate in the sample cell, with the pressure changing throughout the analysis. Also possible is a partial integration mode, where the sample cell is evacuated to a set pressure and a dilution gas is added and maintained in the cell for a period of time, e.g., 1 minute. In some cases, the sample flows through the gas cell and out through an exit valve and multiple spectra are obtained over time by the spectrometry system and possibly averaged for detection limit reduction, i.e., enhancing detection sensitivity. The gas cell can be a partially integrating cell or a flow cell, such as a lightpipe, through which the output from the separator flows. In a flow cell, such as a light pipe, the gas can flow continuously through the cell with a characteristic residence time in the cell. Other operating modes can be employed, such as, for example, a mode that reduces the size of the data set.

As seen above, various configurations of the GC-FTIR analysis system are possible and many of these configurations utilize an evacuated (typically partially) sample cell. The following applies to those embodiments employing an evacuated sample cell or, alternatively, flow cells that are held at low pressure by operation of a vacuum pump or at least at a lower pressure than the outlet of the GC. See, for example, outlet 52 in the FIGURE.

Historical GC-FTIR based on Light Pipe technology had to run the optical pipe at high temperatures to prevent condensation. This caused issues in that the reflectivity of the light pipe was reduced due to the high temperatures required. Thus, the high temperatures (required to prevent condensation) resulted in a loss of signal. Also, the conventional light pipe approach would not have been conducive to the use of TDT tubes because the peak would be broadened too much to get the whole peak in the gas cell.

Even with some multiple pass cell arrangements, the sample cell, a second generation White cell, for example, often had to be heated to a temperature such as 150° C., 200° C., 250° C., 300° C. or higher, to facilitate the analysis of sample components with varying vapor pressures or boiling points, e.g., to measure semi-volatile or even nearly non-volatile compounds.

It is also noted here that in the approaches described in U.S. Pat. No. 9,606,088 or U.S. Patent Application Publication No. 2017/0122920, if a compound were to enter the gas cell and condense, it would be observed in the spectra due to a loss of the compound with time and a negative peak would be seen.

In a configuration in which the volume of the sample cell is appropriately selected (relative to the volume of the sample exiting the GC column), the gas emerging from GC column 48 expands into the detection chamber (gas cell) 100. By doing so, the vapor pressure of the gas can be lower since the volume now occupied by the gas is increased by 500 to 1000 times or more. In some systems, the gas eluting from the GC is expanding from less than 1 milliliter (mL) to 200 mL.

Due to the expansion described above, much more material can stay in the gas phase at 191° C., which is a typical temperature for the gas cell. Without the expansion, SVOCs exiting the GC at a temperature of, for example, 350° C. would be expected to condense upon reaching a sample cell held at 191° C. To prevent condensation, the sample cell would require raised temperatures, leading to complications in the IR spectral analysis and the loss in gold reflectivity already discussed.

It is known that the vapor pressure of a substance increases non-linearly with temperature according to the Clausius-Clapeyron relation. The atmospheric pressure boiling point of a liquid (also known as the normal boiling point) is the temperature at which the vapor pressure equals the ambient atmospheric pressure.

The Antoine equation is a mathematical expression of the relation between the vapor pressure and the temperature of pure liquid or solid substances. The basic form of the equation is:

$$\text{Log } P = A - B/(C+T)$$

where T is the temperature of the substance and A, B and C are substance specific coefficients.

A corresponding plots, such as for example, a Vapor Pressure Versus Temperature Chart, uses a linear horizontal axis and a logarithmic vertical axis to produce slightly curved lines, so that one chart can graph several liquids, in this case methyl chloride, butane, neo-pentane, diethyl ether, methyl acetate, fluorobenzene, and 2-heptene. According to these plots, the atmospheric vapor pressure goes up by ~1 order per every 50° C. increase.

Based on these considerations, the vapor pressure of materials of interest here is expected to decrease by about 3 orders (for a lower temperature of about 150° C. and a high temperature of about 350° C.). The cell volume however is increasing by about or more than 3 orders of magnitude. These conditions can support the loss in vapor pressure of the lower temperature without SVOC's condensing in the sample cell 100. As a consequence, very low level detection (parts per trillion) of semi volatile organic compounds (SVOCs) become possible.

In some embodiments, the TDTs employed (see, e.g., TDT 24 in the FIGURE) use an inexpensive packing material such as, for instance, glass wool. In addition to lower costs, this type of packing will not collect VOCs and/or water and will easily release the trapped SVOCs.

In one example, samples are collected on TDTs with large sample volumes, e.g., 1,000 L of sample, through a ¼ inch TDT packed with glasswool or a like material to trap only SVOCs. The TDT is then heated to desorb the SVOC's, which are analyzed in GC column 48 and sample cell 100 as described above.

As far as the samples are concerned, many SVOCs are collected from dust samples or other sources. Traditionally, they are then extracted with methylene chloride, hexane and the like to concentrate enough material to observe the compounds. In embodiments described herein, samples can be collected on TDTs and solvent extraction is not required. In one example, samples are collected from air and give a better estimate of the true contamination.

The following discussion considers some specific examples and operating parameters.

A chart of compounds and their approximate heat of sublimation are listed below as referenced from the following article: Enthalpies of sublimation and vapour pressures of 11 polycyclic hydrocarbons, C. G. De Kruif, *J. Chem. Thermodynamics* 1980, 12, 243-248.

The enthalpy of sublimation is the energy required to take the material from a solid state directly into the vapor phase, usually expressed in J/mol or kJ/mol. Nearly all materials, even very non-volatile ones, exhibit some vapor pressure at room or elevated temperatures. This means they can pass through a properly configured gas chromatograph at below the boiling point and be detected in the vapor phase.

Using the $\Delta H°$ values of sublimation found in the reference article the approximate maximum concentrations of each material were calculated using the Clausius-Clapeyron equation for two temperatures. The first temperature is 191° C. (464K) which is the typical gas cell temperature of the analyzers discussed above. The second temperature is 300° C. (573K) which is a common detector temperature or maximum GC column temperature.

Ratios of the two concentrations were calculated. In most cases the value was less than 1,000, suggesting that expansion of the gas from the GC column with a volume under 1 mL, to a cell of approximately 200 mL will allow the material to stay in the gas phase even with a lower temperature. In many implementations, the gas emerging from the GC column expands from an initial volume at the outlet of the GC column to a sample cell having a volume that is at least 100, 200, 500, 1,000 or more larger.

Some of the compounds shown here have some of the highest potential boiling points that are traditionally measured by GC, with 5 that are over 700K (427° C.) and one that is 984K (711° C.). Even with a boiling point 500° C. higher than the gas cell temperature, these compounds can be measured due to the expansion into the gas cell that is approximately 500 times larger than the portion of the GC column in which the gas initially resides.

Also, for most of these compounds, if collected from air samples and concentrated, their specific concentration in the GC will be well less than their maximum concentration at 300° C.

A chart of ΔH° of sublimation, sample temperatures and approximate maximum concentrations is shown in the table below:

| Compound | ΔH° J/Mol | T(ΔH°) K | Boiling Point K | Sample Temp MAX Detector K | Est. Max Conc. ~ppm(@191 C.) | Max. Sample Temp-GC Exit K | Est. Max Conc. ~ppm(@300 C.) | Δ Max Concentrations 300 C./191 C. |
|---|---|---|---|---|---|---|---|---|
| Naphthalene | 74,400 | 268 | 491 | 464 | 346,269 | 573 | 13,574,575 | 39.2 |
| Phenanthrene | 90,500 | 325 | 613 | 464 | 3,338 | 573 | 289,498 | 86.7 |
| Anthracene | 100,400 | 351 | 613 | 464 | 1,789 | 573 | 252,787 | 141 |
| 1,2-benzoanthracene | 113,100 | 386 | 711 | 464 | 37.73 | 573 | 9972 | 264 |
| Chyrsene | 118,900 | 406 | 721 | 464 | 16.93 | 573 | 5957 | 352 |
| 1,2:3,4-dibenzoanthracene | 139,100 | 440 | 759 | 464 | 0.820 | 573 | 781 | 953 |
| triphenylene | 115,600 | 395 | 984 | 464 | 0.133 | 573 | 40 | 299 |
| 1,2:5,6-dibenzoanthracene | 148,800 | 449 | 797 | 464 | 0.100 | 573 | 154 | 1537 |
| pentacene | 154,000 | 513 | 798 | 464 | 0.055 | 573 | 110 | 1986 |

As already discussed, the multiple reflection modified "White Cell" utilized in the gas cell often employs gold reflecting optics and it is known that as the temperature rises the reflectivity of gold decreases. Thus, a lower gas cell temperature can assure that more light will pass through the gas cell and produce lower potential detection limits.

Also, since IR gases have absorption spectra that depend on temperature, it is ideal to choose a single temperature at which to run the detector so that the collected sample spectra are only measured at one temperature and will match the quantified spectral library without having to vary the gas cell temperature with time or for a specific list of compounds.

Nonetheless, if an application required a higher temperature, the gas cell can effectively operate up to about 250° C. and spectral calibrations could be collected at this temperature to meet the new requirement.

As a result, in some embodiments, the sample cell 100 is held at a lower temperature than the GC. In one examples, the gas cell is held at about 250° C. or lower, such as less than 200° C. On the other hand, GC column 48 is held at greater than 250° C., such as greater than 300° C.

While this invention has been particularly shown and described with references to preferred embodiments thereof, it will be understood by those skilled in the art that various changes in form and details may be made therein without departing from the scope of the invention encompassed by the appended claims.

What is claimed is:

1. A sample analysis method, comprising:
   directing a sample that includes one or more SVOC components to a GC column to temporally resolve components present in the sample;
   expanding output gas from the GC column into a sample cell,
   wherein the sample cell is held at a temperature lower than the temperature of an outlet of the GC column and has a pressure lower than the pressure at the outlet of the GC column,
   and wherein the sample cell has a volume sufficiently large for maintaining the one or more SVOC components in a gaseous phase; and
   obtaining infrared spectra of the components in the sample cell with a Fourier transform infrared spectrometry system.

2. The sample analysis method of claim 1, further comprising maintaining background infrared spectra that include infrared spectra from previously eluted components and analyzing currently eluting components with reference to the background infrared spectra.

3. The sample analysis method of claim 1, wherein spectral responses of the components are acquired over time and current spectral responses are compared to a background that changes with time and comprises previously acquired spectral responses.

4. The sample analysis method of claim 1, further comprising collecting the one or more SVOC components on a concentrating device.

5. The sample analysis method of claim 4, wherein the concentrating device is a thermal desorption tube packed with a material that does not trap water or volatile organic compounds.

6. The sample analysis method of claim 1, wherein the outlet of the GC column is at a temperature that is at least about 200° C. higher than the temperature of the sample cell.

7. The method of claim 1, wherein the volume of the sample cell is at least about 200 times higher than an initial volume available to the gas before emerging from the outlet of the GC column.

8. The method of claim 1, wherein the one or more SVOC is present in an air, water or solid sample.

9. The method of claim 1, wherein the sample contains a pesticide, a herbicide, an insecticide, a plasticizer, a flame retardant, a phthalate, a mycotoxin, a PCB, an illicit drug, an explosive or an accelerant.

10. The method of claim 1, wherein the one and more SVOCs are not concentrated by solvent extraction.

11. The method of claim 1, wherein IR calibration spectra are established at an initial temperature of the sample cell.

12. The method of claim 11, wherein the sample cell is heated from the initial temperature to an intermediate temperature, wherein the intermediate temperature is lower that the temperature of the outlet of the GC column.

13. The method of claim 12, wherein additional IR calibration spectra are obtained at the intermediate temperature.

14. The method of claim 1, wherein the sample cell is fitted with gold-coated optics and the temperature of the sample cell is sufficiently low to substantially preserve IR reflectivity of the gold-coated optics.

15. The method of claim 1, wherein detection levels for the one or more SVOCs are as low as parts per trillion.

16. The method of claim 1, wherein the sample cell is evacuated prior to expanding the output gas from the GC column.

17. The method of claim 1, wherein the sample cell is a flow cell held at a pressure that is lower than atmospheric pressure.

* * * * *